(12) United States Patent
Heggeness (10) Patent No.: US 7,931,679 B2
(45) Date of Patent: Apr. 26, 2011

(54) BONE COMPRESSION DEVICE

(75) Inventor: Michael H. Heggeness, Bellaire, TX (US)

(73) Assignee: Baylor College of Medicine, Houston, TX (US)

( * ) Notice: Subject to any disclaimer, the term of this patent is extended or adjusted under 35 U.S.C. 154(b) by 245 days.

(21) Appl. No.: 12/241,512

(22) Filed: Sep. 30, 2008

(65) Prior Publication Data

US 2009/0157122 A1 Jun. 18, 2009

Related U.S. Application Data

(60) Continuation of application No. 11/428,693, filed on Jul. 5, 2006, now abandoned, which is a division of application No. 10/273,853, filed on Oct. 17, 2002, now Pat. No. 7,115,129.

(60) Provisional application No. 60/344,980, filed on Oct. 19, 2001.

(51) Int. Cl.
*A61B 17/70* (2006.01)
*A61B 17/58* (2006.01)
(52) U.S. Cl. ............... 606/280; 606/286; 606/301
(58) Field of Classification Search ............ 606/280, 606/281, 282, 284, 286, 301, 60, 70, 71, 606/77, 105
See application file for complete search history.

(56) References Cited

U.S. PATENT DOCUMENTS 4,219,015 A 8/1980 Steinemann
(Continued)

FOREIGN PATENT DOCUMENTS

WO WO 01/26566 A1 4/2001

OTHER PUBLICATIONS

Nunamaker, David M., et al., A Radiological and Histological Analysis of Fracture Healing Using Prebending of Compression Plates, Clinical Orthopaedics and Related Research, Jan.-Feb. 1979, pp. 167-174, No. 138, J.B. Lippincott Company.

(Continued)

*Primary Examiner* — Pedro Philogene
(74) *Attorney, Agent, or Firm* — Carter, DeLuca, Farrell & Schmidt, LLP (57) ABSTRACT

The invention relates to bone compression devices and bone compression systems, and in particular, to bone compression devices and systems for use in connection with vertebrae. The bone compression devices and bone compression systems are disposed, or installed, along at least one bone to maintain the at least one bone in a desired spatial relationship. Broadly, the invention is directed to a bone compression device for placing in communication with at least one bone having a bone radius of curvature, the bone compression device comprising a plate having a pre-formed shape, a deformed shape, and at least one elastic shape therebetween, the pre-formed shape having a preformed radius of curvature less than the bone radius of curvature, the deformed shape having a deformed radius of curvature greater than the bone radius of curvature, and at least one of the at least one elastic shapes having an elastic radius of curvature that substantially corresponds to the bone radius of curvature. The invention is also directed to a bone compression system wherein the plate includes a string attached to each end of the plate and a tensioner for facilitating the movement of the plate from the pre-formed shape to the at least one elastic shape. Methods of maintaining a bone in a spatial relationship and methods of contouring the bone compression devices are also disclosed.

19 Claims, 7 Drawing Sheets

U.S. PATENT DOCUMENTS

| | | | |
|---|---|---|---|
| 4,263,904 A * | 4/1981 | Judet | 606/74 |
| 4,651,724 A | 3/1987 | Berentey et al. | |
| 4,683,878 A | 8/1987 | Carter | |
| 5,053,036 A | 10/1991 | Perren et al. | |
| 5,147,361 A | 9/1992 | Ojima et al. | |
| 5,180,381 A | 1/1993 | Aust et al. | |
| 5,246,443 A * | 9/1993 | Mai | 606/78 |
| 5,298,115 A | 3/1994 | Leonard | |
| 5,364,399 A | 11/1994 | Lowery et al. | |
| 5,423,826 A | 6/1995 | Coates et al. | |
| 5,549,612 A | 8/1996 | Yapp et al. | |
| 5,601,553 A | 2/1997 | Trebing et al. | |
| 5,603,713 A | 2/1997 | Aust et al. | |
| 5,620,443 A | 4/1997 | Gertzbein et al. | |
| 5,662,655 A | 9/1997 | Laboureau et al. | |
| 5,843,082 A | 12/1998 | Yuan et al. | |
| 5,904,683 A | 5/1999 | Pohndorf et al. | |
| RE36,221 E | 6/1999 | Breard et al. | |
| 5,951,557 A | 9/1999 | Luter | |
| 6,036,693 A | 3/2000 | Yuan et al. | |
| 6,059,787 A * | 5/2000 | Allen | 606/75 |
| 6,066,140 A | 5/2000 | Gertzbein et al. | |
| 6,083,224 A | 7/2000 | Gertzbein et al. | |
| 6,139,550 A | 10/2000 | Michelson | |
| 6,139,551 A | 10/2000 | Michelson et al. | |
| 6,152,927 A | 11/2000 | Farris et al. | |
| 6,190,388 B1 | 2/2001 | Michelson et al. | |
| 6,193,720 B1 | 2/2001 | Yuan et al. | |
| 6,193,721 B1 | 2/2001 | Michelson | |
| 6,214,006 B1 | 4/2001 | Metz-Stavenhagen | |
| RE37,161 E | 5/2001 | Michelson et al. | |
| 6,228,085 B1 | 5/2001 | Theken et al. | |
| 6,248,106 B1 | 6/2001 | Ferree | |
| 6,254,603 B1 | 7/2001 | Gertzbein et al. | |
| 6,273,889 B1 | 8/2001 | Richelsoph | |
| 6,293,949 B1 * | 9/2001 | Justis et al. | 606/279 |
| 2001/0010000 A1 | 7/2001 | Gertzbein et al. | |
| 2001/0020169 A1 | 9/2001 | Metz-Stavenhagen | |

OTHER PUBLICATIONS

Ramotowski, Witold, et al., Zespol An Original Method of Stable Osteosynthesis, Clinical Orthopaedics and Related Research, Nov. 1991, pp. 67-75, No. 272.

Dick, Jeffrey C., et al., Notch Sensitivity of Titanium Alloy, Commercially Pure Titanium, and Stainless Steel Spinal Implants, Spine, 2001, pp. 1668-1672, vol. 26, No. 15, Lippincott Williams & Wilkins, Inc.

Chapter 21 Surgical Management of Cervical Disc Disease, The Spine, 4th Edition, 1999, pp. 497-564, W.B. Saunders Co., Philadelphia, Pennsylvania.

* cited by examiner

BONE COMPRESSION DEVICE

CROSS REFERENCE TO RELATED APPLICATIONS

This application is a continuation of co-pending U.S. patent application Ser. No. 11/428,693, filed Jul. 5, 2006, which is a division of U.S. patent application Ser. No. 10/273,853, filed Oct. 17, 2002, now U.S. Pat. No. 7,115,129, which claims the benefit of U.S. Provisional Patent Application Ser. No. 60/344,980, filed Oct. 19, 2001. Each of these prior applications are incorporated by reference herein in their entirety.

BACKGROUND OF THE INVENTION

1. Field of the Invention

This invention relates to surgical devices, and in particular, to bone compression devices for maintaining bones, namely, one or more vertebrae, in a desired spatial relationship. The invention also relates to methods for maintaining at least one bone in a spatial relationship and methods for contouring the bone compression devices for use in maintaining bones in a desired spatial relationship.

2. Description of Related Art

The use of bone compression devices in connection with vertebrae are known in the art. Many of these prior bone compression devices are directed to fusing together two or more vertebrae. However, the success rate of fusing together four or more levels is extremely low, i.e., approximately 50% as compared to approximately 95% for two level fusion and 98%-99% for single level fusion. At least one reason contemplated for the increase in the percentage of failures of the bone compression devices is that the bone compression devices do not substantially correspond to the anatomical curvature of the bone to which they are applied. Accordingly, prior to installation, or implantation by the surgeon, the bone compression devices must be manipulated or shaped to substantially correspond to the shape of the bone or bones. As the length of the bone compression device increases, e.g., to fuse three or more vertebrae, the amount of manipulation, e.g., bending, required generally increases. As a result of this manipulation, the bone compression device may become permanently deformed, and thus weakened, or experience hysteresis.

As with most all materials used to form surgical implants and devices, e.g., titanium and stainless steel and various alloys, the devices include a pre-formed shape, i.e., the shape of the device as formed during manufacture, and a deformed shape, i.e., the shape of the device after sufficient force is exerted on the device to permanently change the shape of the device. In between the preformed shape and the deformed shape are numerous elastic shapes. These elastic shapes have a tendency to revert back toward the pre-formed shape over a period time ranging from near immediacy, e.g., a few seconds, to a number of weeks or even months. In fact, most materials experience a certain amount of reversion of shape immediately and then, over an extended period of time, experience additional amounts of reversion of shape. This reversion of shape is referred to as hysteresis. One example of hysteresis is illustrated in materials having what has been referred to as "metal memory." Because of hysteresis, many prior bone compression devices do not remain properly shaped and ultimately fail.

Both the weakening of the bone compression device and hysteresis is further complicated by the use of fasteners, e.g., bone screws or bolts, to secure the bone compression devise to the bone. If the fastener holes are misshapen during the manipulation by the surgeon, the fasteners, when installed, generally force the bone compression device back to its original shape, i.e., away from manipulated shape formed by the surgeon to correspond to the shape of the bone.

For example, in one prior approach, the bone compression device is generally straight. Because the spine is lordotic, the bone compression device must be manipulated, or bent, by the surgeon to attempt to shape the bone compression device to correspond to the curvature of the spine. These devices, after implantation, experience hysteresis resulting in the bone compression device attempting to revert back to its pre-formed shape, i.e., straight. As a result, the bone compression device experiences a higher incidence of failure over long lengths. Such hysteresis is increased by the installation of the fasteners into misshapen fastener holes to secure the bone compression device to the bone. As bone screws or other fasteners are inserted to secure the bone compression device to the bone, pressure is placed on the plate to push it onto the bone resulting in the plate straightening out, i.e., being manipulated away from the shape desired by the surgeon.

In another prior approach, the bone compression device is slightly contoured to approximate the curvature of the bone to which the bone compression device is to be connected. However, the pre-formed curvature of the bone compression device rarely, if ever, accurately corresponds to the curvature of the bone to which it is to be implanted. Therefore, the surgeon must still manipulate these bone compression devices to provide additional lordosis or curvature to correspond to the curvature of the bone. While the amount of manipulation by the surgeon may be lessened, these bone compression devices also experience hysteresis resulting in potential failure of the bone compression device.

Accordingly, prior to the development of the present invention, there has been no bone compression device or bone compression system for placing in communication with at least one bone having a bone radius of curvature, methods of maintaining at least two vertebrae in a spatial relationship with each other, or methods of contouring bone compression devices, which: decrease the rate of failure of the bone compression devices due to hysteresis; utilize hysteresis to increase the rate of success of the bone compression devices; decrease the rate of failure of the bone compression devices when employed on long bones or multiple bones, e.g., three or more vertebrae; and provide compressive forces to the bone to which the bone compression devices are implanted, thereby increasing the grip of the bone compression device on the bone. Therefore, the art has sought bone compression devices and bone compression systems for placing in communication with at least one bone having a bone radius of curvature, methods of maintaining at least two vertebrae in a spatial relationship with each other, and methods of contouring bone compression devices, which: decrease the rate of failure of the bone compression devices due to hysteresis; utilize hysteresis to increase the rate of success of the bone compression devices; decrease the rate of failure of the bone compression devices when employed on long bones or multiple bones, e.g., three or more vertebrae; and provide compressive forces to the bone to which the bone compression devices are implanted, thereby increasing the grip of the bone compression device on the bone. It is believed that the present invention will achieve these objectives and overcome the disadvantages of other compression devices and bone compression systems for placing in communication with at least one bone having a bone radius of curvature, methods of maintaining at least two vertebrae in a spatial relationship with each other, and methods of contouring bone compression devices in the field of the invention, but its results or effects are still dependent upon the skill and training of the operators and surgeons.

SUMMARY OF INVENTION

In accordance with the invention, the foregoing advantages have been achieved through the present bone compression device for placing in communication with at least one bone having a bone radius of curvature, the bone compression device comprising a plate having a pre-formed shape, the preformed shape having a pre-formed radius of curvature less than the bone radius of curvature.

A further feature of the bone compression device is that the plate may include a deformed shape and at least one elastic shape between the pre-formed shape and the deformed shape, the deformed shape having a deformed radius of curvature greater than the bone radius of curvature, and at least one of the at least one elastic shapes having an elastic radius of curvature that substantially corresponds to the bone radius of curvature. Another feature of the bone compression device is that the plate may include a first end, a second end, and at least two attachment members. An additional feature of the bone compression device is that at least one of the at least two attachment members may be a hole. Still another feature of the bone compression device is that at least one of the at least two attachment members may be a loop. A further feature of the bone compression device is that at least one of the two attachment members may be disposed at the first end of the plate and another of the at least two attachment members may be disposed at the second end of the plate. Another feature of the bone compression device is that at least one of the at least two attachment members is may be hole. An additional feature of the bone compression device is that at least one of the at least two attachment members may be a loop. Still another feature of the bone compression device is that the plate may include a first end, a second end, and at least two attachment members. A further feature of the bone compression device is that the plate may include a length having a longitudinal axis and a width having a lateral axis, the preformed radius of curvature being disposed along the length. Another feature of the bone compression device is that the plate may include a length having a longitudinal axis and a width having a lateral axis, the preformed radius of curvature being disposed along the width. An additional feature of the bone compression device is that the plate may include a first end, a second end, at least two fastener holes disposed near the first end, and at least two fastener holes disposed near the second end.

In accordance with the invention, the foregoing advantages have also been achieved through the present bone compression system for placing in communication with at least one bone having a bone radius of curvature, the bone compression system comprising: a plate having a first end, a second end, a first attachment member, a second attachment member, a pre-formed shape, a deformed shape, and at least one elastic shape between the pre-formed shape and the deformed shape, the pre-formed shape having a preformed radius of curvature less than the bone radius of curvature, the deformed shape having a deformed radius of curvature greater than the bone radius of curvature, and at least one of the at least one elastic shapes having an elastic radius of curvature that substantially corresponds to the bone radius of curvature; a string having a first end and a second end, wherein the first end of the string is releasably secured to the first attachment member and the second end of the string is releasably secured to the second attachment member, and a tensioner having a shaft and a spool, the tensioner facilitating the movement of the plate from the preformed shape to the at least one elastic shape that substantially corresponds to the bone radius of curvature.

A further feature of the bone compression system is that the first and second attachment members may be holes, one hole being disposed at the first end of the plate and the second hole being disposed at the second end of the plate. Another feature of the bone compression system is that the first end and the second end of the string each may include at least one hook. An additional feature of the bone compression system is that the first and second attachment members may be loops, one loop being disposed at the first end of the plate and the second loop being disposed at the second end of the plate. Still another feature of the bone compression system is that the first end and the second end of the string each may include at least one hook. A further feature of the bone compression system is that the tensioner may include at least one plate hole interface member. Another feature of the bone compression system is that the tensioner may include a rachet. An additional feature of the bone compression system is that the first attachment member may be disposed at the first end of the plate and the second attachment member may be disposed at the second end of the plate. Still another feature of the bone compression system is that the plate may include a length having a longitudinal axis and a width having a lateral axis, the pre-formed radius of curvature and the at least one elastic radius of curvature being disposed along the length. A further feature of the bone compression system is that the plate may include a length having a longitudinal axis and a width having a lateral axis, the pre-formed radius of curvature and the at least one elastic radius of curvature being disposed along the width. Another feature of the bone compression system is that the plate may include a first end, a second end, at least two fastener holes disposed near the first end, and at least two fastener holes disposed near the second end.

In accordance with the invention, the foregoing advantages have also been achieved through the present method of contouring a bone compression device for placing in communication with at least one bone having a bone radius of curvature, the method comprising the steps of: providing a bone compression device having a plate, the plate including a first end, a second end, a first attachment member, a second attachment member, a pre-formed shape, a deformed shape, and at least one elastic shape between the pre-formed shape and the deformed shape, the pre-formed shape having a preformed radius of curvature less than the bone radius of curvature, the deformed shape having a deformed radius of curvature greater than the bone radius of curvature, and at least one of the at least one elastic shapes having an elastic radius of curvature that substantially corresponds to the bone radius of curvature; releasably securing a string having a first end and a second end to the first attachment member and the second attachment member of the plate; applying a tensioner having a shaft and a spool to the string; and actuating the tensioner whereby the string is wrapped around the spool and the plate is moved from the pre-formed shape to at least one of the at least one elastic shapes.

A further feature of the method of contouring a bone compression device for placing in communication with at least one bone having a bone radius of curvature is that the string may be releasably secured to the first and second attachment members by passing first end of the string through the first attachment member and tying first end of the sting into a knot, and passing second end of the string through the second attachment member and tying second end of the string into a knot. Another feature of the method of contouring a bone compression device for placing in communication with at least one bone having a bone radius of curvature is that the first and second ends of the string may include first and second hooks, the string being releasably secured to the first and second attachment members by passing the first hook through the first attachment member and passing the second hook through the second attachment member.

In accordance with the invention, the foregoing advantages have also been achieved through the present method of maintaining at least two vertebrae in a spatial relationship with each other, the at least two vertebrae forming a bone radius of curvature, the method comprising the steps of: providing a bone compression device having a plate, the plate including a first end, a second end, a pre-formed shape, a deformed shape, and at least one elastic shape between the pre-formed shape and the deformed shape, the pre-formed shape having a pre-formed radius of curvature less than the bone radius of curvature, the deformed shape having a deformed radius of curvature greater than the bone radius of curvature, and at least one of the at least one elastic shapes having an elastic radius of curvature that substantially corresponds to the bone radius of curvature; contouring the bone compression device by moving the bone compression device from the pre-formed shape to at least one of the at least one elastic shapes corresponding to the bone radius of curvature; disposing the bone compression device along the bone radius of curvature; and securing the bone compression device to the at least two vertebrae.

A further feature of the method of maintaining at least two vertebrae in a spatial relationship with each other is that at least one bone graft may be disposed between the at least two vertebrae prior to securing the bone compression device to the at least two vertebrae. Another feature of the method of maintaining at least two vertebrae in a spatial relationship with each other is that the bone compression device may be contoured to the bone radius of curvature formed by at least three vertebrae. An additional feature of the method of maintaining at least two vertebrae in a spatial relationship with each other is that the bone compression device may be contoured to the bone radius of curvature formed by at least four vertebrae. Still another feature of the method of maintaining at least two vertebrae in a spatial relationship with each other is that the bone compression device may be contoured to the bone radius of curvature formed by at least five vertebrae. A further feature of the method of maintaining at least two vertebrae in a spatial relationship with each other is that the bone compression device may include a first fastener hole and a second fastener hole disposed near the first end and a third fastener hole and a fourth fastener hole disposed near the second end, the third fastener hole being disposed diagonally with respect to the second fastener hole and the fourth fastener hole being disposed diagonally with respect to the first fastener hole, and wherein the first end is secured to one of the at least two vertebrae with a first fastener inserted through the first fastener hole, the second end is secured to one of the at least two vertebrae with a second fastener inserted through the fourth fastener hole, the first end is further secured to one of the at least two vertebrae with a third fastener inserted through the second fastener hole, and the second end is further secured to one of the at least two vertebrae with a fourth fastener inserted through the third fastener hole.

The bone compression devices and bone compression systems for placing in communication with at least one bone having a bone radius of curvature, methods of maintaining at least two vertebrae in a spatial relationship with each other, and methods of contouring bone compression devices have the advantages of decreasing the rate of failure of the bone compression devices due to hysteresis; utilize hysteresis to increasing the rate of success of the bone compression devices; decreasing the rate of failure of the bone compression devices when employed on long bones or multiple bones, e.g., three or more vertebrae; and providing compressive forces to the bone to which the bone compression devices are implanted, thereby increasing the grip of the bone compression device on the bone. As mentioned above, it is believed that the present invention will achieve these objectives and overcome the disadvantages of other surgical devices and surgical systems and methods in the field of the invention, but its results or effects are still dependent upon the skill and training of the operators and surgeons.

While the invention will be described in connection with the preferred embodiment, it will be understood that it is not intended to limit the invention to that embodiment. On the contrary, it is intended to cover all alternatives, modifications, and equivalents, as may be included within the spirit and scope of the invention as defined by the appended claims.

DETAILED DESCRIPTION AND SPECIFIC EMBODIMENTS

The present invention is directed to bone compression devices and bone compression systems for maintaining at least one bone in a desired spatial relationship. While the description of the bone compression devices, bone compression systems, and methods of contouring the bone compression devices will be directed to use in connection with two or more vertebrae, it is to be understood that the bone compression devices, bone compression systems, methods of maintaining at least two vertebrae in a spatial relationship with each other, and methods of contouring the bone compression devices of the invention may be used, or performed, in connection with any bone in which it is desired to maintain, or place, at least one bone in a desired spatial relationship, e.g., the pelvis, the femur, the fibula, the tibia, humerus, ulna, radius, or any other bone. For example, the bone compression devices of the invention may be employed in long bone, e.g., femur, and pelvic fracture fixation. Further, the bone compression device may be used in connection with rigid locked screw-plates and screw-plates that permit some screw subsidence or angulation, both of which are bone compression devices known in the art.

In the preferred embodiments, the bone compression devices are utilized to maintain one or more vertebrae, and more preferably, three or more vertebrae, of the spine, and in particular, the cervical vertebrae of humans, in a desired spatial relationship. In these embodiments, prior to the installation of the bone compression device, one or more bone grafts are generally disposed between two or more vertebrae. As illustrated in FIGS. 1b and 1c, for example, after a disk 26, located between two vertebrae 21, is removed from spine 20, a bone graft 28, e.g., a portion of the patients' own bone, an allograft (portion of bone donated from another individual), or synthetic bone grafts or cages or boxes such as those made from carbon fiber, metal (particularly titanium), or ceramics, is usually disposed in the space created by the removal of the disk 26. Thereafter, the bone compression devices of the invention are installed and secured to at least the vertebra 21 disposed above the graft and the vertebra 21 disposed below the graft. Accordingly, bone graft 28 is compressed between the two vertebrae 21 to maintain bone graft 28 in a spatial relationship with vertebrae 21.

It is contemplated that the bone compression devices of the invention are suitable for fusing, e.g., being secured to, more than three vertebrae having one or more grafts disposed between two or more of the vertebrae. Therefore, in these embodiments, the vertebrae in proximity to the removed disk(s) are maintained in a desired spatial relationship to one another. Therefore, the vertebrae are permitted to heal, and, in some cases, the synthetic bone graft is permitted to be incorporated into the vertebrae using bone growth factors and other biologically active substances to facilitate the growth of bone over the synthetic bone graft.

Figure 1A:
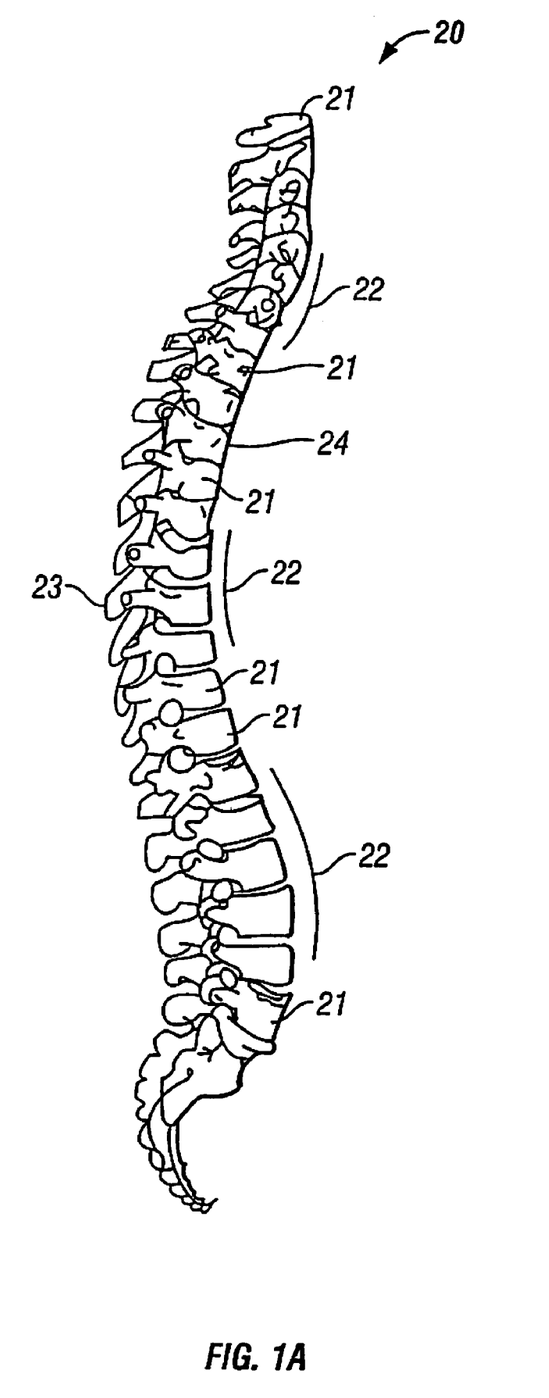
FIG. 1a is a longitudinal side view of a human spinal column.
Figure 1B:
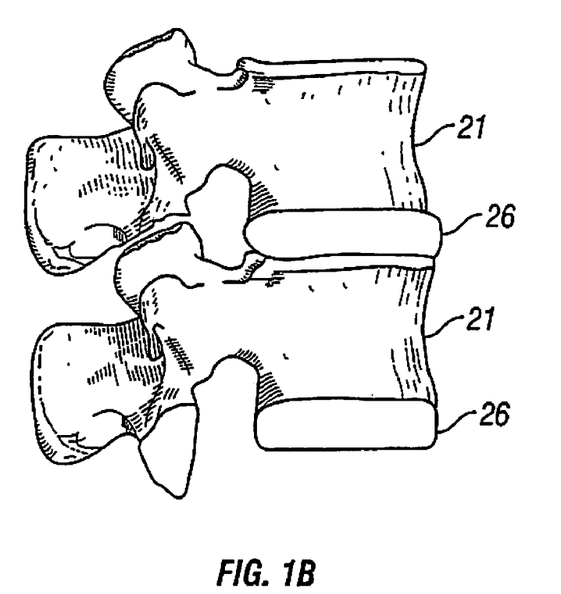
FIG. 1b is a detailed side view of two human vertebrae having a disk disposed between the two vertebrae.
Figure 1C:
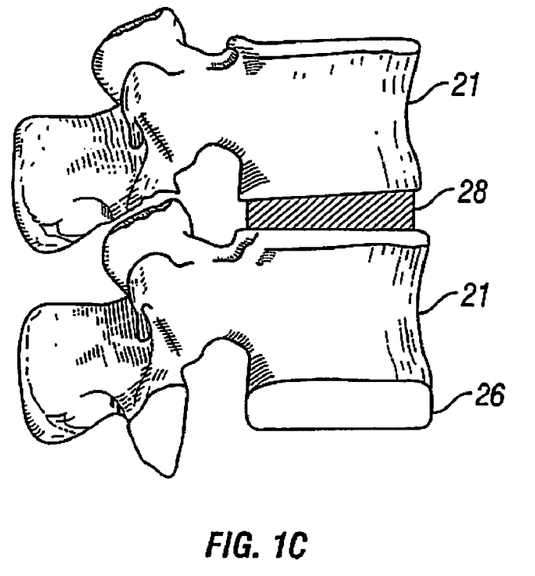
FIG. 1c is a detailed side view of two human vertebrae with a bone graft disposed between two vertebrae.

Referring now to FIG. 1a, spine 20 includes vertebrae 21 and has posterior side 23 and anterior side 24. Spine 20 includes numerous bone radius of curvatures 22 along the longitudinal length of spine 20. As shown in FIG. 1, bone radius of curvatures 22 are identified along anterior side 24 of spine 20. Although the bone compression devices of the invention may be installed, or implanted, along the posterior side 23 of spine 20, generally, bone compression devices are implanted along anterior side 24 of spine 20.

Figure 2:
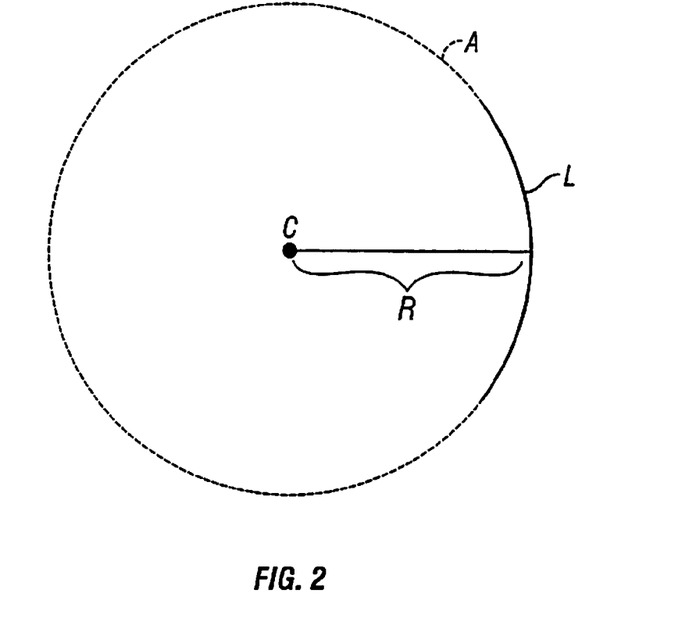
FIG. 2 is a schematic showing the radius of curvature of a longitudinal curve.

Radius of curvature, as used herein referring to the shape of the bone(s) as well as the shape of the bone compression devices and systems, is measured by determining the radius of a circle formed by the longitudinal curve of the bone (bone radius of curvature) or bone compression device (pre-formed radius of curvature, deformed radius of curvature, and elastic radius of curvature) placed along the circumference of the circle formed by the longitudinal curve of the bone or bone compression device. Accordingly, the larger the circle formed by the longitudinal curve of the bone or bone compression device, the larger the corresponding curvature, i.e., the greater the radius of curvature. Therefore, as the longitudinal curve approaches a straight line, the radius of curvature approaches infinity. FIG. 2 illustrates how radius of curvature R is determined along curvature L with respect to circle A having center C.

Figure 3A:
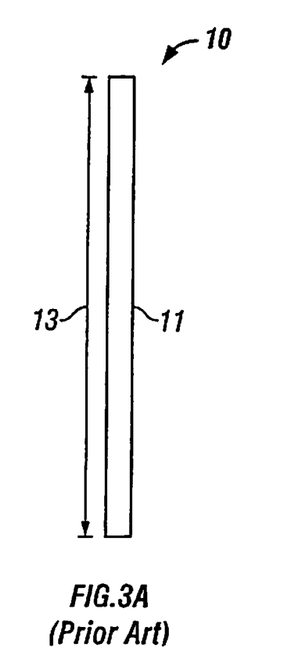
FIG. 3a is a longitudinal side view of a prior art bone compression device before being formed into its implantation shape.
Figure 3B:
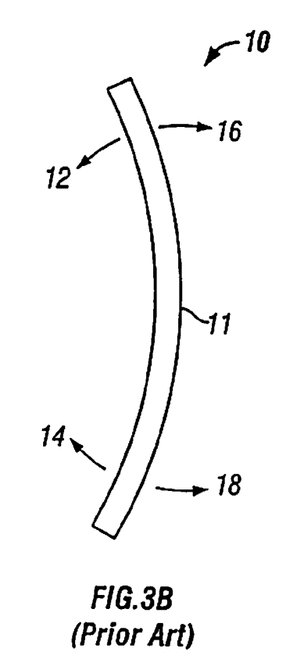
FIG. 3b is a longitudinal side view of the prior art bone compression device shown in FIG. 3a in its implantation shape.

As illustrated in FIGS. 3a and 3b, one prior bone compression device 10 includes plate 11 having longitudinal length 13. As shown in FIG. 3a, plate is generally straight. As such, it must be manipulated, e.g., bent, to correspond to the shape of the bone to which it will be implanted. In other words, bone compression device 10 must be manipulated to correspond to the bone radius of curvature. As shown in FIG. 3b, plate 10 is bent in the direction of arrows 12 and 14 to create the desired radius of curvature. However, due to hysteresis, after plate 11 is bent in this manner plate 11 begins to revert back to its original shape (FIG. 3a) by moving in the direction of arrows 16 and 18. Alternatively, plate 11 is bent to its deformed shape, thereby weakening plate 11.

Referring now to FIGS. 4-7, in one aspect the present invention is directed to bone compression device 40 having plate 50, first end 51, second end 52, upper surface 53, lower surface 54, longitudinal axis 55 along length L of plate 50, and lateral axis 56 along width W of plate 50. Length L and Width W may have any measurement desired or necessary to secure bone compression device 40 the bone(s) desired to be compressed. For example, in embodiments in which three or more vertebrae are desired to be compressed, Length L must be of a distance sufficient to permit attachment of bone compression device 40 to each vertebrae. Therefore, length L of plate 50 will be greater in embodiments in which five vertebrae are to be compressed as compared to embodiments in which only two vertebrae are to be compressed.

Plate 50 also includes at least one fastener hole 58 for receiving fastener (not shown), e.g., bone screws, bolts, etc., to facilitate securing plate 50 to the bone. Preferably, each fastener hole is angled such that each fastener is placed through fastener holes 58 to be secured into the bone at an angle, thereby facilitating securing plate 50 to the bone. Additionally, multiple fastener holes 58 are disposed along the length L and width W of plate 50 as desired or necessary to facilitate securing plate 50 to the bone. For example, in embodiments in which three or more vertebrae are to be secured by bone compression device 40, plate 50 will preferably include fastener holes 58 such that at least one fastener will be inserted and secured to each of the vertebrae. Therefore, the total number of fastener holes 58 will be dependent upon the size of plate 50, the number of bones to be compressed, and the size of the bone(s) to be compressed.

Generally, plate 50 includes at least one fastener hole 58 disposed near first end 51 and at least one fastener hole 58 near second end 52. As shown in FIGS. 4-7, plate 50 preferably includes at least two fastener holes 58 near first end 51 and two fastener holes 58 near second end 52. An advantage of this embodiment is that fasteners, e.g., bone screws, may be place through fastener holes 58 and secured into the bone, and thus securing plate 50 to the bone, in a manner that lessens the torsional resistance of plate 50. For example, a first fastener may be used to secure plate 50 to the bone by placing and securing the fastener through the upper right fastener hole 58 in FIG. 5. Next, a second fastener may be used to secure plate 50 to the bone by placing and securing the fastener through the lower left fastener hole 58 in FIG. 5. A third fastener may then be used to secure plate 50 to the bone by placing and securing the fastener through the upper left fastener hole 58 in FIG. 5. Thereafter, a fourth fastener may be used to secure plate 50 to the bone by placing and securing the fastener through the lower right fastener hole 58 in FIG. 5. All four fasteners may then be tightened as necessary to secure plate 50 to the bone.

Preferably, plate 50 includes plate interface, e.g., plate interface hole 57, for receiving a tool, e.g., tensioner 70 discussed in greater detail below, to facilitate handling of plate 50, moving plate 50 from its pre-formed shape to at least one of its at least one elastic shapes, and placement of plate 50 along the bone.

Figure 4:
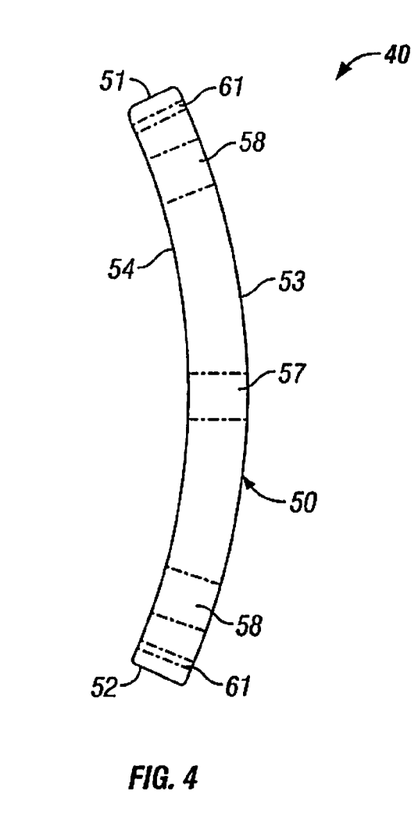
FIG. 4 is a longitudinal side view of a specific embodiment of the bone compression device of the present invention.
Figure 5:
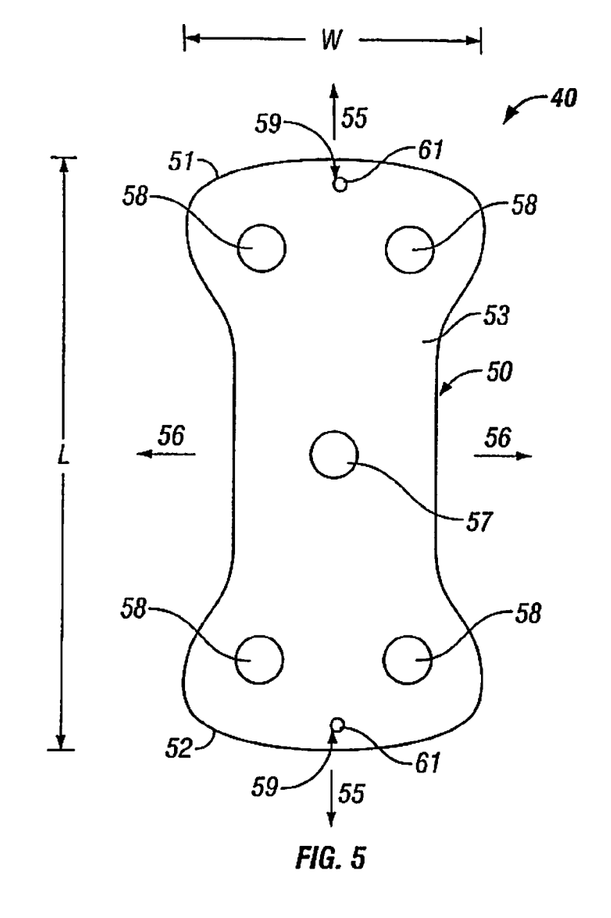
FIG. 5 is a top view of the bone compression device shown in FIG. 4.
Figure 6:
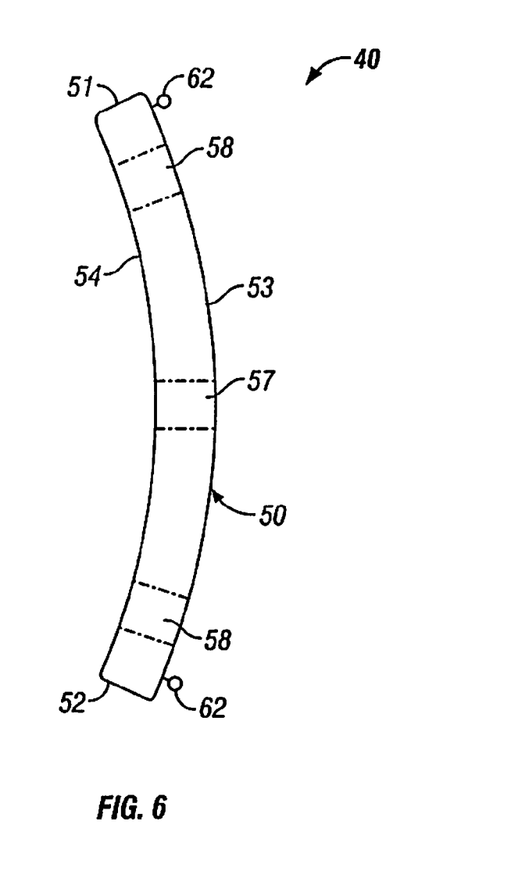
FIG. 6 is a longitudinal side view of another specific embodiment of the bone compression device of the present invention.
Figure 7:
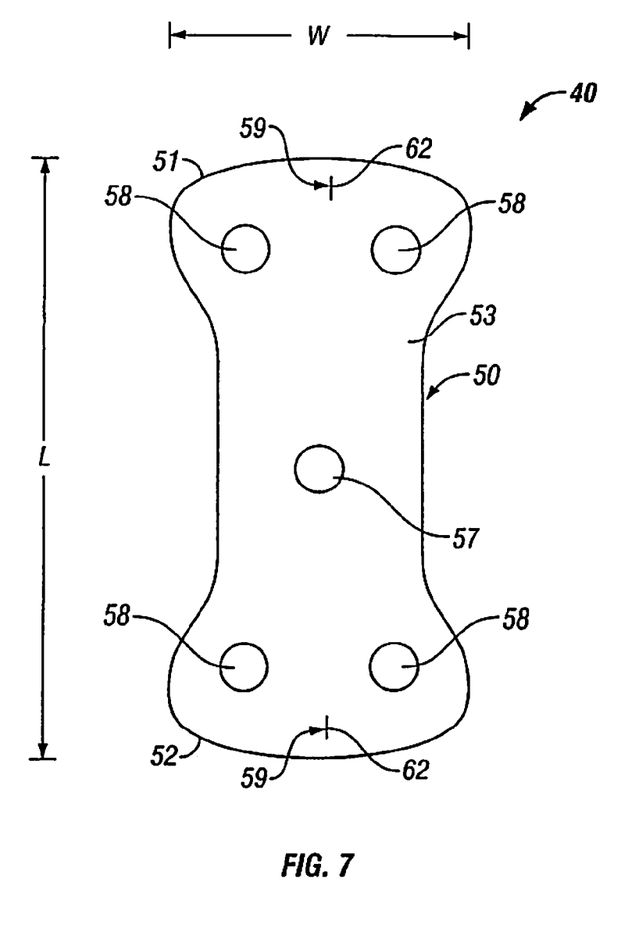
FIG. 7 is a top view of the bone compression device shown in FIG. 6.

Pre-formed radius of curvature, deformed radius of curvature, and each of the at least one elastic radius of curvature therebetween are determined based upon the curvature of plate 50 along longitudinal axis 55 or lateral axis 56. As shown in FIGS. 4 and 6, plate 50 is in its preformed shape having pre-formed radius of curvature defined by the longitudinal curvature of lower surface 54.

Plate 50 preferably includes at least two attachment members 59. In the embodiment shown in FIGS. 4-5, each attachment member 59 is hole 61. In the embodiment shown in FIGS. 6-7, each attachment member 59 is loop 62.

While it is to be understood that the material from which bone compression device 50 is formed may be any material known to persons of ordinary skill in the art, the preferred material is titanium or other material having a relatively low coefficient of elasticity, thereby reducing the total number of elastic shapes bone compression device may take. As is readily apparent to those skilled in the art, the number of elastic shapes the bone compression device may take will depend on the material from which bone compression device is formed. Materials having a high coefficient of elasticity will have many more elastic shapes than a material having a low coefficient of elasticity. Suitable materials include titanium, titanium-vanadium-aluminum, cobalt-chromium-molybdenum, as well as any other alloy, metal, or other material approved by the Food and Drug Administration.

Additionally, plate 50 may have any two or three dimensional shape, size, or thickness desired or necessary to be sufficiently secured to one or more bones.

Figure 8:
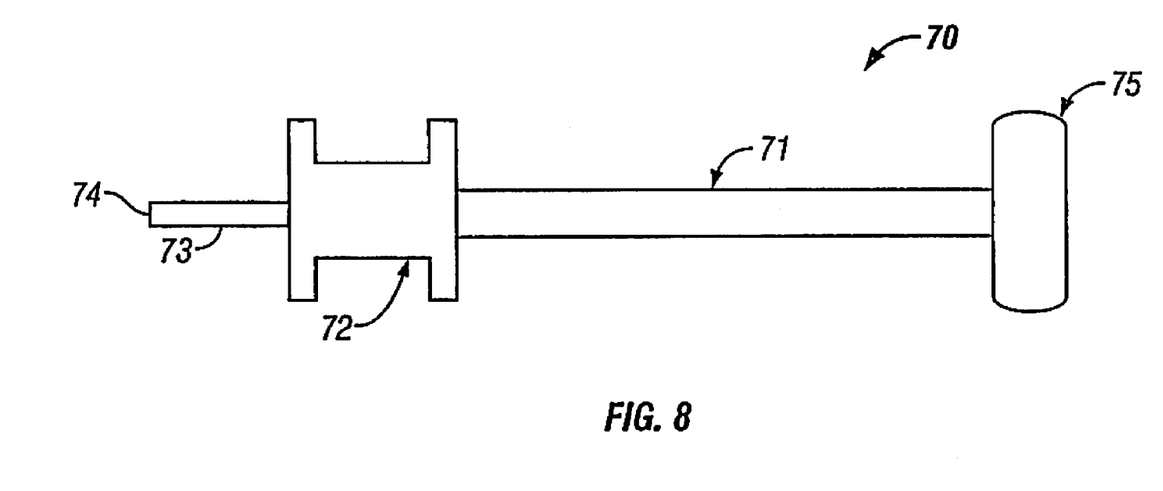
FIG. 8 is a side view of a specific embodiment of the tensioner of one specific embodiment of the bone compression system of the present invention.

As discussed above, plate 50 preferably includes at least two attachment members, e.g., hole 61 or loop 62, for facilitating the contouring of plate 50, for example, by string 80 (FIG. 9) and tensioner 70. As shown in FIG. 8, tensioner 70 includes shaft 71 and spool 72. Spool 72 preferably includes a ratchet (not shown) to further facilitate winding string 80 around spool 72 and applying straightening forces to plate 50. Tensioner 70 also preferably includes at least one plate interface member 73 having interface member end 74 for interfacing with plate 50, e.g., by inserting at least one plate interface member 73 into at least one corresponding plate interface hole 57 disposed along plate 50, to further secure plate 50 to tensioner 70 thereby facilitating placement of plate 50 along the bone as well as tightening string 80 around spool 72. Interface member end 74 preferably is shaped to correspond with the shape of the plate interface. In one embodiment, plate interface hole 57 is a fastener hole 58. Tensioner 70 may also include handle 75 to facilitate gripping and turning tensioner 70 while tightening string 80 around spool 72.

Figure 9:
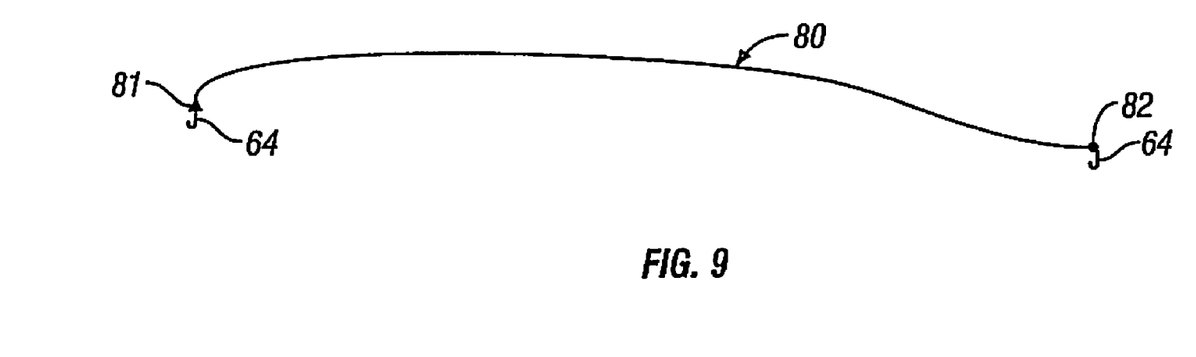
FIG. 9 is a side view of a specific embodiment of the string of one specific embodiment of the bone compression system of the present invention.
Figure 10:
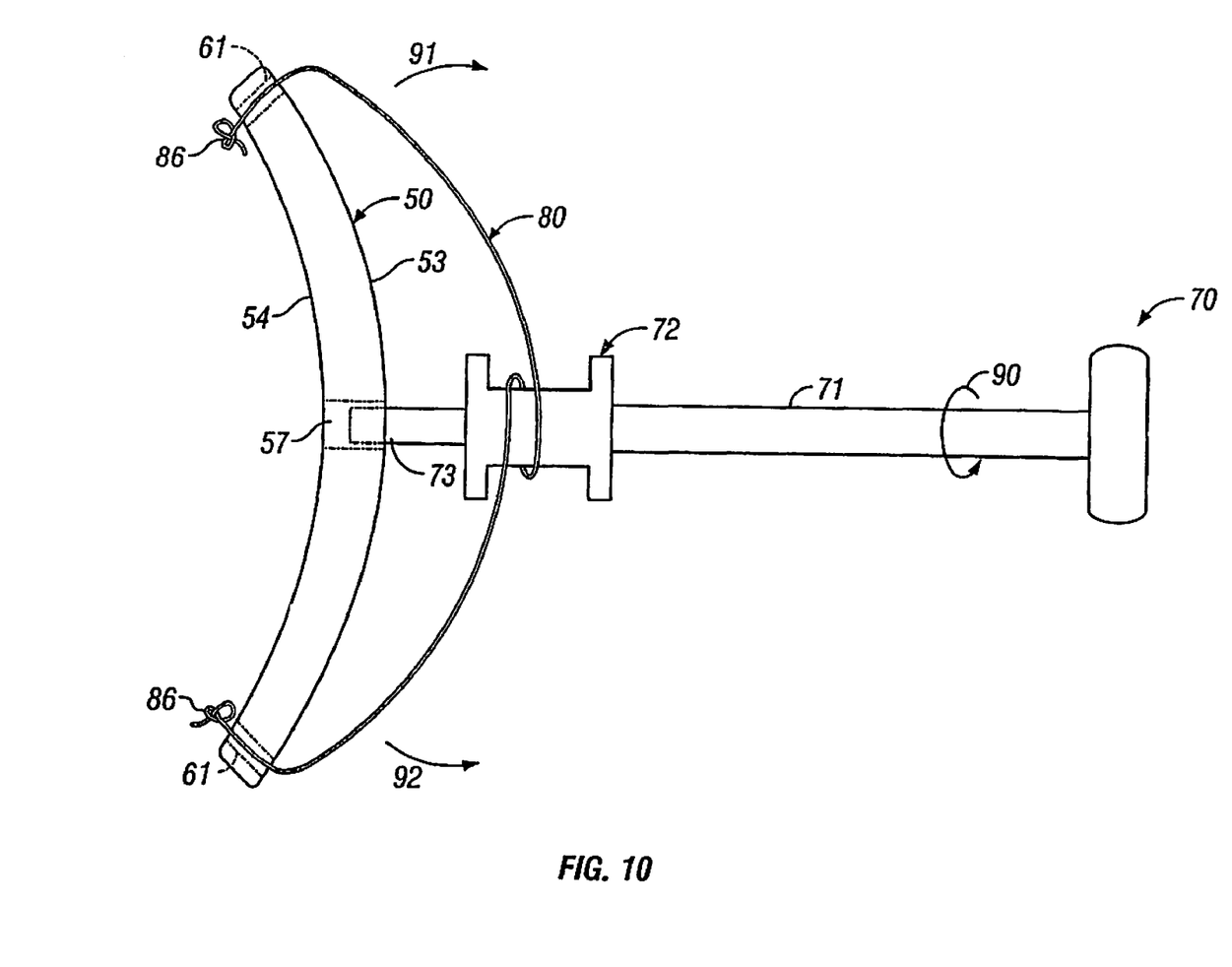
FIG. 10 is side view of one specific embodiment of the bone compression system of the present invention.

As illustrated in FIG. 9, string 80 includes first end 81 and second end 82 and may be releasably secured to plate 50 through any manner known to persons skilled in the art. For example, string 80 may be passed through each attachment member 59 and tied in a knot 86 (FIG. 10). Therefore, after installation of plate 50, each knot may be cut to release plate 50. Alternatively, as shown in FIG. 8, first end 81 and second end 82 of string 80 may include hook 64 to be passed through each attachment member 59 to secure plate 50 during installation. Thereafter, each hook 64 may be removed from each attachment member 59 thereby releasing plate 50.

String 80 may be formed out of any material known to persons skilled in the art provided that string 80 is strong enough to withstand the tensioning forces applied to string 80 during use without breaking. Preferred materials for forming string 80 include Kevlar and other polymers having high tensile strength.

Referring now to FIG. 10, tensioner 70 is placed in contact with plate 50 by inserting plate interface member 73 into plate interface hole 57. First end 81 of string 80 is passed through attachment member 59, i.e., hole 61 in FIG. 10, and tied into knot 86 to secure first end 81 to plate 50. Likewise, second end 82 of string 80 is passed through attachment member 59, i.e., hole 61 in FIG. 10, and tied into knot 86 to secure second end 82 to plate. String 80 is then wrapped around spool 72 of tensioner 70. Tensioner 70 may then be turned in the direction of arrow 90 to wind, or wrap, string 80 around spool 72. In doing so, string 80 exerts forces on plate 50 whereby place 50 is manipulated, or moved, in the direction of arrows 91 and 92 (straightening forces) to at least one of the elastic shapes of plate 50 until the elastic radius of curvature substantially corresponds to the bone radius of curvature, i.e., the implantation shape. Plate 50 may then be installed along one or more bones. After placement of plate 50 along one or more bones, tensioner 70 is turned in the opposite direction of arrow 90. Therefore, due to hysteresis, plate 50 will have a tendency to move in the opposite direction of arrows 91 and 92. In doing so, plate 50 will be further secured to the bone or bones.

In another aspect, the present invention is directed to methods of maintaining a bone in a spatial relationship, and in particular, at least two vertebrae in a spatial relationship with each other utilizing the bone compression devices discussed above. With respect to use of the bone compression devices for maintaining two or more vertebrae is spatial relationship with each other, first, bone compression device 40 is contoured by moving bone compression device 40 from its pre-formed shape to at least one of the at least one elastic shapes corresponding to the bone radius of curvature. The bone radius of curvature is formed by the at least two vertebrae. Bone compression device 40 is then disposed along the bone radius of curvature and secured to the at least two vertebrae.

This method of maintaining at least two vertebrae in a spatial relationship with each other may be used in connection with the insertion of at least one bone graft between the at least two vertebrae prior to securing the bone compression device to the at least two vertebrae. Accordingly, the bone compression devices facilitate maintaining the bone graft between the vertebrae as well as maintaining the at least two vertebrae in a spatial relationship with each other.

It is also noted that the bone compression devices may also be used for maintaining at least three, at least four, and at least five vertebrae in a spatial relationship with each other. Another feature of the method of maintaining at least two vertebrae in a spatial relationship with each other.

The methods of maintaining at least two vertebrae in a spatial relationship with each other may also include steps directed to order in which the fasteners are inserted through the fastener holes 58. For example, in one embodiment, bone compression device 40 includes four fastener holes 58 (FIGS. 4-7). The first fastener hole 58,101 near first end 51 (upper left in FIGS. 5 and 7) is disposed diagonally from fourth fastener hole 58,104 near second end 52 (lower right in FIGS. 5 and 7) and second fastener hole 58,102 near first end 51 (upper right in FIGS. 5 and 7) is disposed diagonally from third fastener hole 58,103 near second end 52 (lower left in FIGS. 5 and 7). A first fastener is then inserted through first fastener hole 58,101 and first end 51 of plate 50 is secured to the bone (one of the at least one vertebrae). A second fastener is then inserted through fourth fastener hole 58,104 and second end 52 of plate 50 is secured to the bone (one of the at least one vertebrae). First end 51 of plate 50 is then further secured to the bone (one of the at least two vertebrae) with a third fastener inserted through second fastener hole 58, 102, and second end 52 of plate 50 is further secured to the bone (one of the at least two vertebrae) with a fourth fastener inserted through the third fastener hole 58,103. It is believed that by inserting the fasteners through the fastener holes 58 to secure plate 50 to the bone in this manner, torsional resistance is lessened, thereby increasing the likelihood that bone compression device 40 will not be loosened over time.

It is to be understood that the invention is not limited to the exact details of construction, operation, exact materials, or embodiments shown and described, as obvious modifications and equivalents will be apparent to one skilled in the art. For example, while the bone compression device illustrated and described above, is discussed in connection with vertebrae, it may be used to with any other individual bone or bones. The dimensions and shapes, as well as the means for attaching the bone compression device to any bone, or number of bones, can be easily determined by a person of ordinary skill in the art. Moreover, while the bone compression devices have been described as being installed on the anterior side of the spine or other bone, the bone compression devices may be installed on the posterior side of the spine or other bone. Additionally, the bone compression devices may be installed on any vertebrae, i.e., lumbar, thoracic, cervical, or sacral. Further, the lower surface of the plate may include projections, or spikes, to facilitate securing the plate to the bone. Moreover, the plate interface member and corresponding plate interface may be any shape desired or necessary to permit the plate interface to securely capture the plate interface and thus permit manipulation and placement of the plate during installation of the plate. Additionally, the bone compression device may lack a distinguishable longitudinal axis, e.g., have a squared shape, or have the pre-formed, deformed, and elastic radii of curvature disposed along the width or lateral axis instead of the length or longitudinal axis. Accordingly, the invention is therefore to be limited only by the scope of the appended claims.

What is claimed:

1. A device to maintain at least two vertebral bodies having a bone radius of curvature along a length thereof in a spatial relationship with each other, comprising:
   a surgical plate having a first portion configured and dimensioned to be attached to a first vertebral body and a second portion configured and dimensioned to be attached to a second vertebral body, the surgical plate having a length and a width, the length being greater than the width, the surgical plate having a first configuration having a first radius of curvature in the lengthwise direction and a second, elastically deformed configuration having a second radius of curvature in the lengthwise direction, the first radius of curvature being less than the bone radius of curvature, the second radius of curvature being greater than the first radius of curvature, the surgical plate in the second configuration being biased toward the first configuration, and the surgical plate in the second configuration adapted to be attached to the first vertebral body at the first portion and to the second vertebral body at the second portion.

2. The device of claim 1, wherein the surgical plate first portion includes at least one fastener aperture adapted to receive a fastener and the surgical plate second portion includes at least one fastener aperture adapted to receive a fastener.

3. The device of claim 2, further comprising at least one bone fastener configured and dimensioned to engage bone through the first aperture and at least one bone fastener configured and dimensioned to engage bone through the second aperture.

4. The device of claim 3, wherein the least one fasteners are each selected from the group consisting of bone screws and bolts.

5. The device of claim 1, wherein the surgical plate further includes first and second attachment members, the first and second attachment members operably coupled to a tensioner configured to transition the surgical plate from the first configuration to the second configuration.

6. The device of claim 5, wherein at least one of the attachment members is selected from the group consisting of: a loop and an aperture.

7. The device of claim 1, wherein surgical plate includes an elastic state between the first configuration and the second configuration.

8. The device of claim 7, wherein the elastic state is configured to maintain the first vertebral body and the second vertebral body in a predetermined spatial relationship.

9. A bone compression system for placing in communication with at least one bone having a bone radius of curvature along a length thereof, the bone compression system comprising:
   a plate having a first end, a second end, a first attachment member, a second attachment member, a first shape, a second shape, and at least one elastic shape between the first shape and the second shape, the first shape having a first radius of curvature less than the bone radius of curvature, the second shape having a second radius of curvature greater than the bone radius of curvature, and the at least one elastic shape having an elastic radius of curvature that substantially corresponds to the bone radius of curvature;
   a string having a first end and a second end, wherein the first end of the string is releasably secured to the first attachment member and the second end of the string is releasably secured to the second attachment member; and
   a tensioner having a shall and a spool, wherein the string wraps around the spool so as to facilitate the movement of the plate from the first shape to the at least one elastic shape that substantially corresponds to the bone radius of curvature.

10. The bone compression system of claim 9, wherein the first and second attachment members are holes, a first hole being disposed at the first end of the plate and a second hole being disposed at the second end of the plate.

11. The bone compression system of claim 10, wherein the first end and the second end of the string each include at least one hook.

12. The bone compression system of claim 9, wherein the first and second attachment members are loops, a first loop being disposed at the first end of the plate and a second loop being disposed at the second end of the plate.

13. The bone compression system of claim 12, wherein the first end and the second end of the string each include at least one hook.

14. The bone compression system of claim 9, wherein the tensioner includes at least one plate hole interface member.

15. The bone compression system of claim 9, wherein the tensioner includes a ratchet.

16. The bone compression system of claim 9, wherein the first attachment member is disposed at the first end of the plate and the second attachment member is disposed at the second end of the plate.

17. The bone compression system of claim 9, wherein the plate includes a length having a longitudinal axis and a width having a lateral axis, the first radius of curvature and the at least one elastic radius of curvature being disposed along the length.

18. The bone compression system of claim 9, wherein the plate includes a length having a longitudinal axis and a width having a lateral axis, the first radius of curvature and the at least one elastic radius of curvature being disposed along the width.

19. The bone compression system of claim 9, wherein the plate includes a first end, a second end, at least two fastener holes disposed near the first end, and at least two fastener holes disposed near the second end.

* * * * *